United States Patent [19]

Walsh

[11] Patent Number: 4,545,888

[45] Date of Patent: Oct. 8, 1985

[54] APPARATUS FOR ELECTROPHORETIC RECOVERY OF NUCLEIC ACIDS AND OTHER SUBSTANCES

[76] Inventor: J. William Walsh, 3823 Beech Ave., Baltimore, Md. 21211

[21] Appl. No.: 597,677

[22] Filed: Apr. 6, 1984

[51] Int. Cl.[4] ............................................. G01N 27/28
[52] U.S. Cl. ................................ 204/301; 204/299 R; 204/182.8
[58] Field of Search ........... 204/180 G, 299 R, 180 R, 204/301

[56] References Cited

U.S. PATENT DOCUMENTS

| | | | |
|---|---|---|---|
| 3,384,564 | 5/1968 | Ornstein et al. | 204/299 R |
| 3,791,950 | 2/1974 | Allington | 204/299 R |
| 3,795,600 | 3/1974 | Allington | 204/299 R |
| 3,847,785 | 11/1974 | Allington | 204/299 R |
| 3,867,271 | 2/1975 | Hoefer | 204/299 R |
| 4,048,049 | 9/1977 | Hoefer | 204/299 R |
| 4,284,491 | 8/1981 | Vesterberg | 204/299 R |

FOREIGN PATENT DOCUMENTS

WO81/02790 10/1981 PCT Int'l Appl. .

*Primary Examiner*—Andrew H. Metz
*Assistant Examiner*—B. J. Boggs, Jr.
*Attorney, Agent, or Firm*—Walter G. Finch

[57] ABSTRACT

The invention is an improved electrophoresis device for the recovery of nucleic acids and other substances. The apparatus and method of this invention is for the purpose of recovering large charged molecules in a pure state after they have been separated from a mixture by gel electrophoresis; the charged molecules from gels which has high quantitative recovery without contamination by an apparatus and method which is rapid and convenient to use. The apparatus consists of a plurality of transfer chambers suitably supported in a vessel for containing an aqueous buffer solution, a plurality of filter discs for support of a layer of DEAE cellulose resin in the bottom of the transfer chambers, a plurality of negative electrodes (one in each of the upper portion of each of the transfer chambers), a positive electrode for placement in the buffer which will surround the plurality of transfer chambers, and a power supply.

10 Claims, 10 Drawing Figures

APPARATUS FOR ELECTROPHORETIC RECOVERY OF NUCLEIC ACIDS AND OTHER SUBSTANCES

BACKGROUND AND SUMMARY OF THE INVENTION

The invention relates to recovery methods and apparatuses and in particular to methods and apparatuses for recovery by electrophoresis methods and devices. Specifically, it relates to a method and apparatus for the recovery of nucleic acids and other substances.

Electrophoresis of large charged molecules, such as deoxyribonucleic acid (DNA) fragments, has been an established laboratory method for approximately 20 years. In its most common form, an electric field is imposed between opposite ends of a thin slab of gel. A sample, containing a mixture of various charged molecules, such as DNA fragments, is introduced into one end of the gel. The electric field causes the DNA fragments to migrate to the opposite end of the gel. The velocity at which each DNA fragment migrates is dependent upon its mobility, a characteristic determined by the DNA fragment's length, shape, and other characteristics. Fragments having similar mobility will migrate as a band at a given velocity. With time, the sample will be separated into distinct bands, each composed of like fragments.

By means of staining or radioactive tagging, the various DNA fragments can be located and identified. As described above, electrophoresis is a simple and sensitive analytical technique. The recovery of the DNA fragments from the gel following electrophoresis has historically been difficult. Some of the methods that have been utilized are described hereinafter.

The crush and soak method: the gel material containing the DNA fragment to be recovered is excised from the gel slab and is ground or crushed. Soaking the crushed gel for long periods of time in a salt solution, extracts the DNA fragment from the gel. The resulting DNA fragment is then ethanol precipitated from the salt solution. The recovery efficiency by this method is quite low.

The melting agarose/chemical extraction method: the gel material containing the DNA fragment to be recovered is excised from the gel slab and is melted at about 65 degrees centigrade. Phenol extraction is followed by organic chemical purification. The recovery efficiency by this method is relatively low and the purification procedures are long and labor intensive.

Blitz blotting method: in this method, the entire gel slab is placed in contact against a sheet of DEAE cellulose paper, which is known for its ability to bind DNA fragments. This sandwich is then immersed in a buffer solution and by electrophoretic means, all the bands are transferred from the gel to the DEAE paper. This method has a relatively high recovery efficiency, but the apparatus is costly and cumbersome.

DEAE insertion in gel method: in this method, slots are cut in the gel immediately "downstream" of each of the bands. DEAE paper is inserted into the slots and by means of electrophoresis, the bands are driven inbo the DEAE paper. This method is extremely technique dependent. Cutting the slot deforms the electric field which causes varying portions of the band to be driven around the slot.

Electro-elution/dialysis membrane method: in this method, the gel material containing the DNA fragment to be recovered is excised from the gel slab and is immersed in the buffer solution in the apparatus. An electric field elutes the DNA fragment into the buffer and onto a dialysis membrane where it is recovered by washing. A major drawback is that all molecules above a certain size are deposited on the dialysis membrane. The DNA fragment may irreversibly bind to the membrane.

Gel decomposition/glass beads method: the gel material containing the DNA fraction is decomposed by chemical means and the resulting mixture, in a buffer, is poured over glass beads which are removed and washed. The DNA is eluted from the glass beads with a salt solution. Fair recovery efficiency with large molecules. Buffer conditions are very critical.

Each of the described prior art methods has disadvantages in either efficiency, ease, purity, or cost. Consequently, there is a need for a method combining the following characteristics: high quantitative recovery efficiency of biologically functional charged molecules free of contaminants; a simple setup; a rapid and unattended operation; and a relatively low cost. The present invention accomplishes this.

The present invention provides new and improved apparatus, as well as an improved method, for the recovery of charged molecules from gels which has a high quantitative recovery without contamination and the mechanism is rapid and convenient to use. As developed the apparatus is durable, inexpensive to obtain and to operate. For purposes of this specification the description refers to nucleic acids. It is to be understood, however, that it is within the scope and intent of the invention to utilize it for the recovery of other substances, such as proteins.

The apparatus consists of a plurality of transfer chambers, preferably of an inert and non-conductive plastics which are suitably supported in a vessel for containing an aqueous buffer solution, a plurality of filter discs for support of a layer of DEAE cellulose resin (one disc for each transfer chamber), a plurality of negative electrodes (one in each of the upper portion of the transfer chambers), a positive electrode for placement in the buffer which will surround the plurality of transfer chambers, and a power supply. Other refinements of the apparatus structure will be described hereinafter.

In operation, the gel containing the DNA to be recovered is excised from the gel slab and sliced into conveniently sized pieces for placement in the transfer chambers. The filter disc for supporting the layer of DEAE cellulose resin is in the bottom of each of the transfer chambers. The negative electrodes are placed in contact with the buffer in the upper portion of each of the transfer chambers. The positive electrode is placed in contact with the buffer that surrounds the plurality of transfer chambers.

The buffer permeates the filter and bed of DEAE to form a continuous conductive path for the flow of an electrical current between the electrodes. An orifice at the bottom of each of the transfer chambers restricts the electical current flow to the center of the bed of DEAE to assure passage of the electrical current through the DEAE.

When the power supply is activated, an electrical field is established in each transfer chamber. Positively charged molecules are attracted to each of the negative electrodes and vice versa. The negatively charged DNA fragments within the gel, under influence of the electrical field, begin to migrate through the gel and toward the path to the positive electrode.

After exiting the gel, the DNA fragments continue to migrate through the buffer toward the orifice. On passing through the DEAE, the DNA fragments are brought into intimate contact with the DEAE resin and are bound to the surface of the DEAE resin, which has a very specific binding affinity for DNA.

To recover the DNA, each of the transfer chambers is removed and allowed to drain. Following washing, the DNA is eluted from the DEAE by established procedures using the appropriate salt solution.

It is, therefore, an object of this invention to provide an apparatus for recovery of charged molecules from gels which has a high quantitative recovery without contamination.

It is also an object of this invention to provide an apparatus that is an improved electrophoresis device for the recovery of nucleic acids.

It is another object of this invention to provide an apparatus that has a simple setup.

It is still another object of this invention to provide an apparatus that has a rapid and unattended operation.

It is yet another object of this invention to provide an apparatus that is relatively low in cost.

Further objects and advantages of the invention will become more apparent in light of the following description of the preferred embodiments.

DESCRIPTION OF THE PREFERRED EMBODIMENTS

Figure 1:
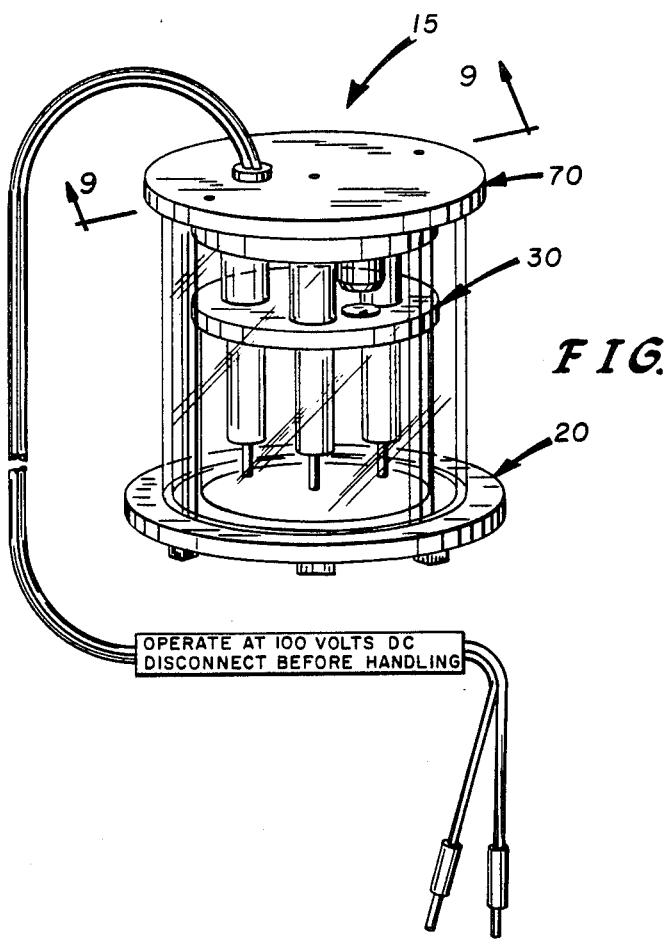
FIG. 1 is a pictorial view of an assembled apparatus for the recovery of nucleic acids.
Figure 2:
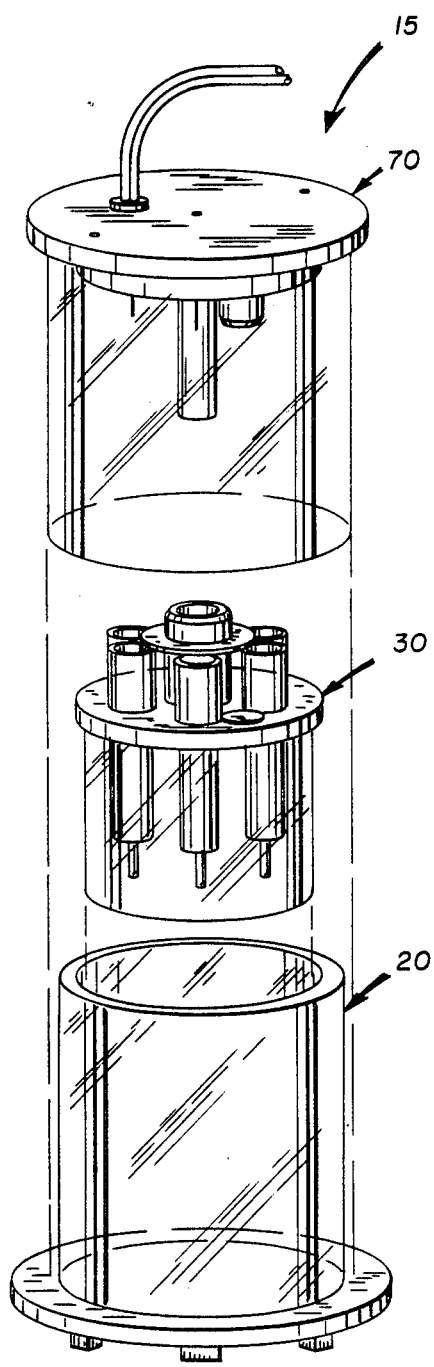
FIG. 2 is an exploded view of the components of FIG. 1.

Referring now to the drawings, and particularly to FIGS. 1 and 2, an apparatus for recovery of nucleic acids is shown at 15. FIG. 1 is a pictorial view and FIG. 2 is an exploded view of the three major components which compose the apparatus for recovery of nucleic acids 15. Hereinafter the apparatus for recovery of nucleic acids 15 will be referred to as apparatus 15.

The three major components shown in FIG. 2 which compose the apparatus 15 are the base container component 20, the assembled transfer chambers and support component 30, and the electrode component 70. Details of the three components will be described hereinafter as well as the method for using the apparatus 15 for the recovery of nucleic acids.

Figure 3:
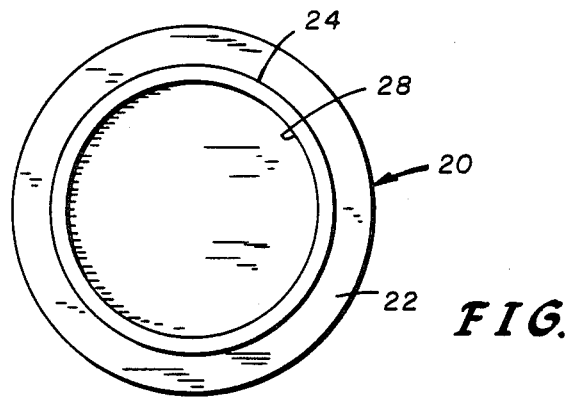
FIG. 3 is a plan view of the base container component for an apparatus for the recovery of nucleic acids.
Figure 4:
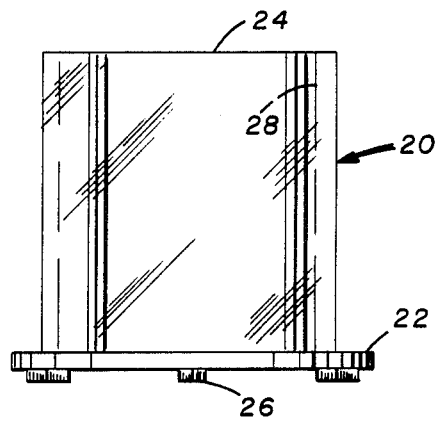
FIG. 4 is a side elevation of FIG. 3.

Turning now to FIGS. 3 and 4, the details of the base container component 20 is described hereinafter. The base container component 20 consists of a circular base 22, a cylindrical wall 24 suitably affixed to the circular base 22, and a plurality of feet or legs 26 suitably affixed to the exterior or bottom of the circular base 22. The base container component is liquid tight and capable of holding and containing a liquid therein.

The cylindrical wall 24 has an inside diameter 28 which inside diameter 28 is of a sufficient size to removably receive the assembled transfer chambers and support component 30 as hereinafter described. Likewise, the external or outside diameter of the cylindrical wall 24 is of such a size so that it will telescopingly and removably loosely fit inside of a portion of the electrode component 70 as hereinafter described.

The cylindrical wall 24 is suitably affixed to the circular base 22, such as by an adhesive, however, it is to be understood that it is within the scope and intent of this invention to affix the cylindrical wall 24 to the circular base 22 by other suitable bonding means or methods, or even to monolithically mold the cylindrical wall 24 and circular base 22 as a single integral unit. The cylindrical wall 24 has a thickness to provide for rigidity as well as a thickness to affix to the thickness of the circular base 22.

The plurality of feet or legs 26 may be of rubber or other suitable material suitably affixed, as by an adhesive, to the circular base 22. It is to be understood however, that the plurality of feet or legs 26 may be monolithically molded as an integral part of the circular base 22 within the scope and intent of this invention. It is especially noted that the use of a plurality of feet or legs 26 of a rubber or rubber-like material having a non-skid type surface is advantageous to prevent the apparatus 15 from sliding on a surface, particularly if the surface might be disturbed by external vibration.

Figure 5:
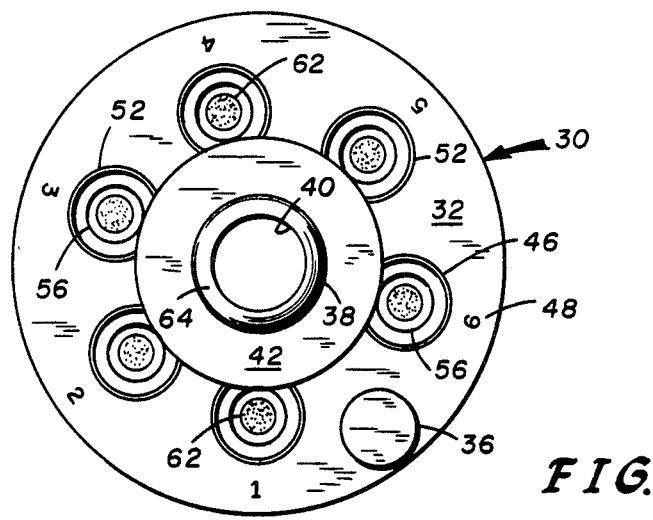
FIG. 5 is a plan view of the assembled transfer chambers and support component for an apparatus for the recovery of nucleic acids.
Figure 6:
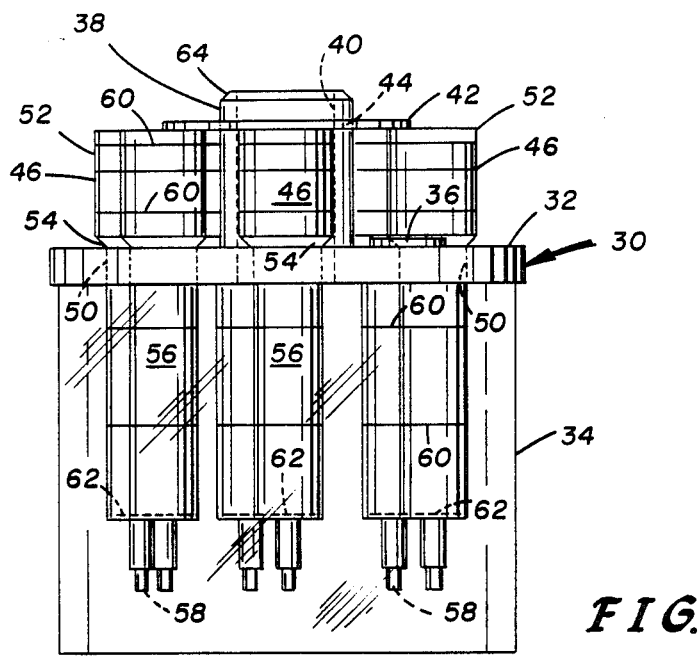
FIG. 6 is a side elevation of FIG. 5.

Turning now to the assembled transfer chambers and support component 30 shown in FIGS. 5 and 6, hereinafter referred to as the transfer chambers component 30, the transfer chambers component 30 consists of: a circular support plate 32, a cylindrical support wall 34, an alignment key means 36, a cylindrical support means 38, a hold-down or securing means 42, a plurality of transfer chambers 46 and a plurality of filter means 62.

The circular support plate 32 is suitably assembled and affixed to the cylindrical support wall 34, such as by an adhesive, and to the cylindrical support means 38, such as by an adhesive. It is to be understood that it is within the scope and intent of this invention to suitably affix the circular support plate 32, cylindrical support wall 34, and the cylindrical support means 38 to each other by other suitable means, including monolithically molding them as an integral unit.

The circular support plate 32, cylindrical support wall 34, and cylindrical support means 38 each have a thickness suitable for providing rigidity.

The circular support plate 32 has a plurality of apertures 50 spaced apart radially around and through the circular plate 32. The plurality of apertures 50 are for receiving and holding the plurality of transfer chambers 46 as hereinafter described.

Opposite each of the plurality of transfer chambers 46 on the uppermost surface of and adjacent to the periphery of the circular support plate 32, the numerals "1" through "6" are stamped or pressed sequentially into the surface of the circular support plate 32, to indicate the designated sequential index or identification 48 number of each of the plurality of transfer chambers 46. It is to be understood, however, that although six transfer chambers 46 are shown in the drawings for purposes of illustration, any number of transfer chambers 46 may be used and that this is within the scope and intent of the invention.

It is to be further understood that although certain elements of the components of this invention hereinbefore and hereinafter are described as being circular or cylindrical, any other geometrical configuration is within the scope and intent of this invention.

The alignment key means 36, preferably of a different color, but not necessarily so required, is located between two adjacent transfer chambers 46 on the uppermost surface of and near the periphery of the circular support plate 32. The alignment key means 36 as shown is circular and flat and suitably affixed to the uppermost surface of the circular support plate 32, such as by an adhesive.

It is to be understood, however, that the alignment key means 36 may be otherwise located or otherwise configured, and may be otherwise affixed to the circular support plate 32, including monolithically molding as an integral part of the circular support plate 32, and that such variations are within the scope and intent of this invention.

As shown in the drawings, the index or alignment key means 36 is located between transfer chambers 46 at the sequential identification or index 48 numerals "1" and "6", and it will be noted that the arc distance between these two adjacent transfer chambers 46 is slightly greater than the arc distance between any other two adjacent transfer chambers 46. The purpose of this is to provide clearance for a matching alignment means in the electrode component 70 as described hereinafter. However, it is to be understood that variation of the above mentioned arc distance or making it the same as the arc distance between any other two adjacent transfer chambers 46 is within the scope and intent of this invention.

The cylindrical support wall 34 is affixed to the lowermost surface of the circular support plate 32 and the cylindrical support means 38 is affixed to the uppermost surface of the circular support plate 32.

An aperture, having the same inside diameter as the inside diameter 40 of the cylindrical support means 38, is centrally located on and through the circular support plate 32. The periphery of the inside diameter 40 of the cylindrical support means 38 coincides with the periphery of the centrally located aperture on and through the circular support plate 32 and, in effect, the aperture through the circular support plate 32 becomes an extension of the passageway, defined by the inside diameter 40, through the cylindrical support means 38. Thus the centrally located aperture through the circular support plate 32 communicates with the passageway, defined by the inside diameter 40, of the support means 38.

The support means 38 has a beveled edge 64 at the distal end thereof for assisting in guiding the distal end of the support means 38 into a recess in the electrode component 70 as hereinafter described.

The support means 38 has a groove 44 cut into the external side thereof to receive, hold and support the hold-down or securing means 42. The groove 44 is so located in the external side of the support means 38 so that the lowermost surface of the hold-down or securing means 42 will substantially be so located so as to hold-down or secure the plurality of transfer chambers 46 in the plurality of respective apertures 50 in the circular support plate 32. The hold-down or securing means 42 may be rubber or rubber-like material or any similar flexible material which can be deformed or pulled aside temporarily and easily to insert or remove any one of or all of the transfer chambers 46 from the apertures 50, without the need for removing the entire hold-down or securing means 42 from the groove 44.

The plurality of transfer chambers 46 are each configured in a series of reduced diameters of the overall length with a passageway therethrough from one end to the other end as described hereinafter. Each transfer chamber 46 has an upper portion 52, a tapered transition portion 54, a lower portion 56, and an orifice portion 58.

The uppermost edge of the upper portion 52 interfaces with the lowermost surface of the hold-down or securing means 42. The tapered transition portion 54 centrally locates the transfer chamber 46 in the aperture 50. The lower portion 56 extends through the aperture 50 and into the interior space of the surrounding cylindrical support wall 34. The orifice portion 58 is wholly within the interior space of the surrounding cylindrical support wall 34.

The upper portion 52 has the largest inside and outside diameters, the tapered transition portion 54 reduces the inside and outside diameters of the upper portion 52 to a smaller inside and outside diameter of the lower portion 56. At the bottom of the lower portion 56 the end is nearly closed by a bottom or floor-like end with a small centrally located aperture therein that leads into and communicates with the reduced diameter of the orifice portion 58.

The passageway through the transfer chamber 46 communicates from the open uppermost end of the upper portion 52 successively downwardly through the upper portion 52, the tapered transition portion 54, the lower portion 56, through the centrally located aperture in the bottom of the lower portion 56, and then through the orifice portion 58 and out through a small orifice-like aperture in the lowermost end of the orifice portion 58.

At the lowermost end of the lower portion 56, of each of the transfer chambers 46, one of the plurality of filter means 62 is located in the lower portion 56 and rests on the aforementioned bottom or floor-like end of the lower portion 56. The filter means 62, such as fiberglass, lies just above and over the small orifice-like aperture in the lowermost end of the lower portion 56.

Ring-like volume lines 60, at spaced intervals may be marked, cut, or molded on to or into the peripheral surface of the upper and lower portions 52 and 56, respectively, of each of the transfer chambers 46 for measurement purposes. It is to be understood, however, that omission of the volume lines 60 is within the scope and intent of this invention, or that the volume lines may be on the inside or on the outside surface of the transfer chambers 46. The increments of the volume lines may be for any volume selected for measuring or recording purposes.

When the transfer chambers component 30 is removably placed into the base container component 20, the outside diameter of the circular support plate 32 fits loosely within the inside diameter 28 of the cylindrical wall 24. The lowermost edge of the cylindrical support wall 34 interfaces with and rests upon the uppermost surface of the circular base plate 22. This arrangement can be seen in FIG. 9.

In such a position the lowermost or distal end of the orifice portion 58 of each of the transfer chambers 46 is located spaced from the uppermost surface of the circular base plate 22; the uppermost or distal end of the cylindrical support means 38 is located just below or spaced from the plane of the uppermost edge of the cylindrical wall 24.

Figure 7:
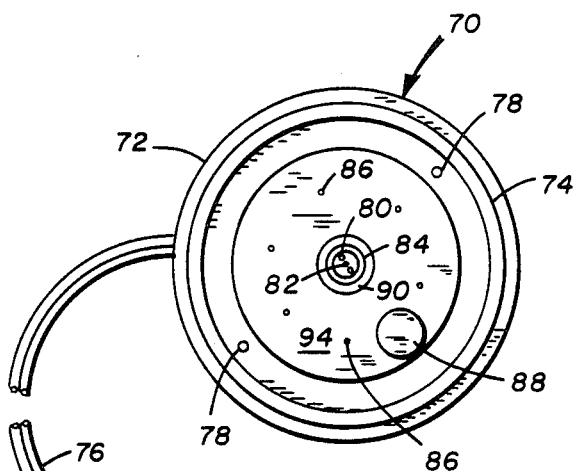
FIG. 7 is a bottom view of the electrode component for an apparatus for the recovery of nucleic acids.
Figure 8:
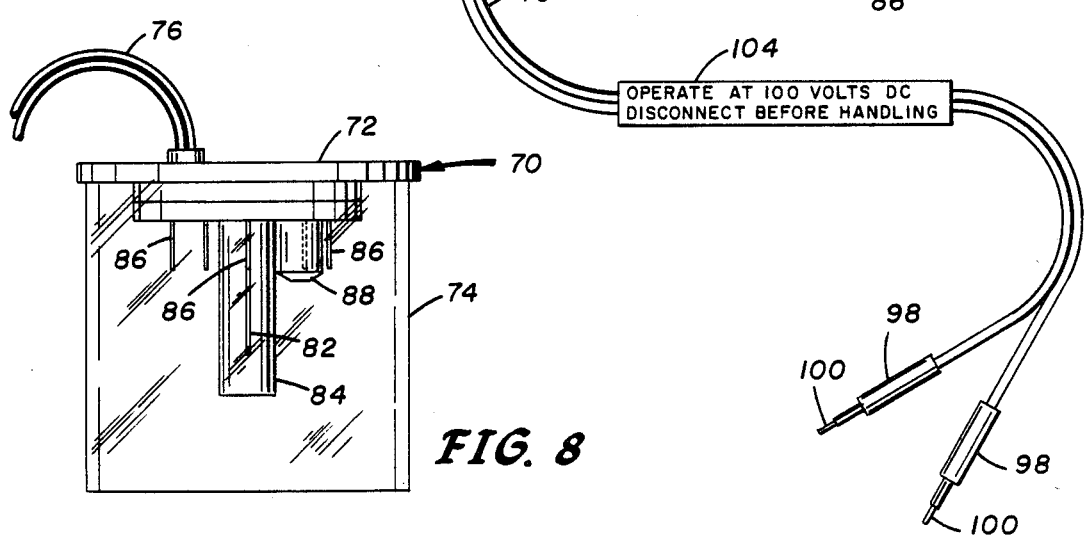
FIG. 8 is a side view of FIG. 7.

Turning now to FIGS. 7 and 8 for a description of the electrode component 70; FIG. 7 shows a bottom or underside view of the electrode component 70 in order to show the detail of the elements, FIG. 8 shows a side elevation of FIG. 7.

The electrode component 70 consists of a circular top plate 72, a cylindrical wall 74, power supply leads 76, a centrally located positive electrode 82, a shield 84 for the positive electrode 82, a plurality of negative electrodes 86, an alignment key 88 to match and mate with alignment key 36 of transfer chambers component 30, and a carrier 94 for electrical connections from the power supply leads 76 to the positive electrode 82 and to the plurality of negative electrodes 86.

The circular top plate 72 and the cylindrical wall 74 are suitably assembled and affixed to each other by suitable means, such as by an adhesive. It is to be understood that it is within the scope and intent of this invention to suitably affix the circular top plate 72 to the cylindrical wall 74 by other suitable means, including monolithically molding them as an integral unit.

The circular top plate 72, the cylindrical wall 74, and the carrier 94 (described hereinafter), each have a thickness suitable for providing rigidity.

Figure 9:
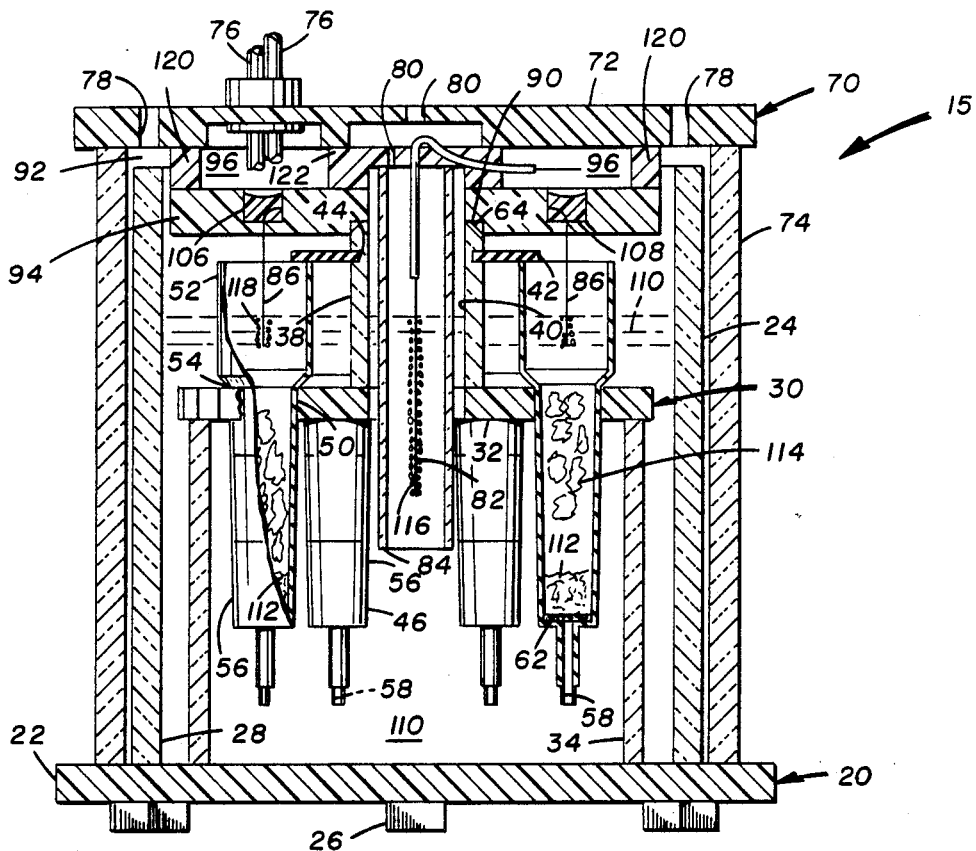
FIG. 9 is a cross-sectional view on line 9—9 of FIG. 1.

In connection with the carrier 94, reference should be made to the cross-sectional view of the apparatus 15 shown in FIG. 9 in order to note the cavity area 96 between the carrier 94 and the circular top plate 72. It is in this cavity area 96 that the electrical wiring connections are made between the power supply leads 76 and the positive and negative electrodes 82 and 86, respectively.

Because of the cross-sectional nature of FIG. 9 the direct connections between the power supply 76 and the positive and negative electrodes 82 and 86, respectively, cannot be shown fully. Essentially, as can be noted in FIG. 10, described hereinafter, the plurality of negative electrodes 86 are electrically connected to the negative lead of the power supply leads 76, and the positive electrode 82 is connected to the positive lead of the power supply leads 76.

Figure 10:
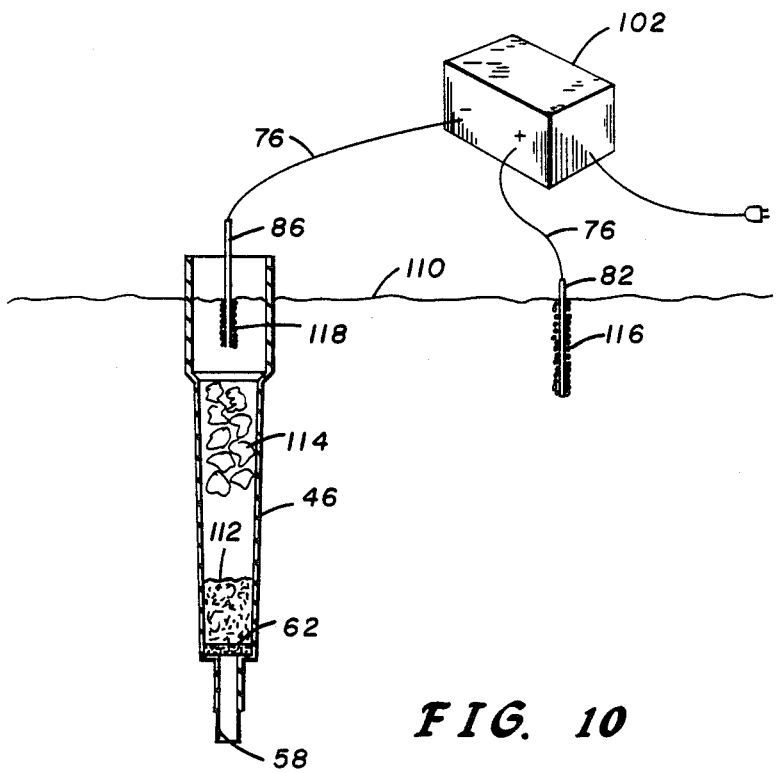
FIG. 10 is an enlarged partial cross-section view of a single transfer chamber, for an apparatus for the recovery of nucleic acids, in schematic relation to a power source.

The positive and negative leads of the power supply leads 76 can be seen in partial section in FIG. 9 passing through the top plate 72. Also, note that the external leads of the power supply leads 76 are secured by a strain relief means retained in the circular top plate 72. For identification the positive and negative leads are preferably insulated in red and black, respectively. As shown in FIG. 7, the positive and negative leads of the power supply 76 are shown with insulated finger grips 98 at their ends and with terminal ends 100 for plugging into the power source 102 as shown in FIG. 10. A binder or short jacket piece 104 collects and maintains the two leads together for easy handling. The binder or short jacket piece 104 carries a notice to "Operate at 100 volts DC, Disconnect Before Handling".

It is to be understood that it is within the scope and intent of this invention to completely jacket the positive and negative leads of the power supply leads 76 instead of the short binder or jacket piece 104.

As can be noted in FIG. 9, the negative electrodes 86 (each extending through the carrier 94) are wired together by wiring that lies in a circular groove 106 that runs around the uppermost surface of carrier 94 and then is electrically connected to the negative lead of the power supply leads 76. The wiring to the plurality of negative electrodes 86 is then sealed in place in the groove 106 with a layer of epoxy resin 108. The electrical connection to the single positive electrode 82 passes through an aperture in the center spacer disc 122 of the carrier 94 and is then electrically connected to the positive lead of the power supply leads 76. The center spacer disc 122 secures the positive electrode 82 in place.

Note in FIG. 9 that the cavity area 96 between the circular carrier 94 and the lowermost surface of the circular top plate 72 is determined by an outer circular spacer ring 120.

Thus, the carrier 94 is suitably assembled and affixed to its outer spacer ring 120 and the centrally located center spacer disc 122, such as by an adhesive, and then suitably affixed to the underside of the circular top plate 72, such as by an adhesive. The center spacer disc 122 is assembled over a centrally located aperture through the circular carrier 94 which, in turn establishes the recess 90 as described hereinafter.

It is to be understood that the assembly and affixing of the circular carrier 94 to the outer spacer ring 120 and to the center spacer disc 122 may be suitably affixed by other suitable means, including monolithically molding them as an integral unit. Thereafter the assembled carrier 94 with the circular spacer ring 120 and the center spacer disc are suitably affixed to the underside of the circular top plate 72, such as by an adhesive.

Note in FIG. 9 that suitable recesses may be cut into the underside of the circular top plate 72 to accommodate the connection of the power supply leads 76 thereto, and to facilitate the wiring from the positive electrode 82.

A plurality of vents 78 are provided by apertures in and through the circular top plate 72 to permit the escape of oxygen gas 118 which is created around the negative electrodes 86 during operation of the apparatus 15.

In a similar manner a plurality of vents 80 through the circular top plate 72 and the center spacer 122 are provided to facilitate the escape of hydrogen gas 116 which is created around the positive electrode 82 during operation of the apparatus 15.

The shield 84 for the centrally located positive electrode 82 is also centrally located and set into the center spacer disc 122 and suitably affixed thereto, such as by an adhesive.

It can be noted in FIG. 9 that the aforementioned assembly of the circular carrier 94 with the center spacer disc 122 creates a recess 90 around the shield 84. This permits the bevel 64 on the top of the distal end of the cylindrical support means 38 to conveniently center the transfer chambers component 30 when the electrode component 70 is added to complete the final assembly of the apparatus 15.

It can also be noted in FIG. 9 that with the assembly and affixing of the circular carrier 94 and its outer spacer ring 120 to the underside of the circular top plate 72, a peripheral recess 92 is created around the carrier 94. When the electrode component 70 is assembled to complete the apparatus 15, the cylindrical wall 24 is removably and loosely telescoped within the inside diameter of the cylindrical wall 74, of the electrode component 70, and the topmost edge of the cylindrical wall 24 fits into the peripheral recess 92 described hereinbefore, thus completing the assembly of the apparatus 15.

In FIG. 9 note that the plurality of peripheral vents 78 communicate the peripheral recess 92 with the atmosphere.

In order to properly align the electrode component 70 with the transfer chambers component 30, the alignment key 88 is suitably affixed to the underside of the carrier 94 such as by an adhesive, in a comparable position to the alignment key 36, described hereinbefore in conjunction with the transfer chambers component 30.

The size of the alignment key 88 is larger than the alignment key 36 and is purposely so such that as it descends in a direction toward the alignment key 36 it may be off center. If so the larger size of the alignment key 88 will bring it to rest upon the top of an adjacent transfer chamber 46. The alignment key 88 is large enough so that it will not drop into or pass into the transfer chamber 46. Furthermore, the height or length of the alignment key 88 is such that in this off center position it is longer than the downwardly projecting negative electrodes 86, (as can be seen in FIG. 8) and thus protects the plurality of negative electrodes 86 from damage until properly located and situated, one negative electrode 86 projecting into each transfer chamber 46.

The bottom or lowermost surface of the alignment key 88 has a slight crown or bevel so that as the electrode component 70 is rotated the alignment key 88 will slide off of the top edge of an adjacent transfer chamber 46 and permit the electrode component 70 to drop into place, safely, so that each negative electrode 86 drops into its respective transfer chamber 46.

Turning now to the function and operation of the apparatus 15, the description hereinafter provides the method for the recovery of nucleic acids by the use of apparatus 15. Particular reference is made to FIG. 10 which shows an enlarged partial cross-section view of a single transfer chamber 46 in a schematic relationship to a power source 102. The power supply leads 76 are appropriately connected to the power source 102. The power source 102 is capable of providing direct current, adjustable as to voltage. The description of the method and operation for this single transfer chamber 46 occurs concurrently in each of the plurality of transfer chambers 46 as is partially illustrated in FIG. 9. The method for the recovery of other substances is similar, varying primarily in the chemicals used.

In operation, a voltage of 100 volts direct current (DC) has been found to be the optimum. At this voltage, with the appropriate aqueous buffer 110 solution, such as TBE buffer solution the current draw is approximately two milliamperes per transfer chamber 46 and the power dissipated is 0.2 watts per transfer chamber 46. The extremely low power consumption eliminates the risk of thermal degradation of the DNA and allows unattended operation.

When the electrode component 70 is removed, the positive and negative electrodes, 82 and 86 respectively, are lifted from the aforementioned buffer 110 and the circuit is automatically broken or disconnected. Furthermore, the cylindrical wall 74, and the shield 84 serve to prevent or shield the user from an electrical shock hazard if the electrode component 70 is removed or lifted while the power is in the "on" position. The power should always be shut "off" at the power source 102 when making a disconnect.

While the apparatus 15 is in operation gases are produced at the positive and negative electrodes, 82 and 86 respectively. Hydrogen gas bubbles 116 at the positive electrode 82, and oxygen gas bubbles 118 at the negative electrodes 86. These gases rise to the surface of the buffer 110 and are vented to the atmosphere as hereinbefore described. The vents 78 and 80 have spaced apart excape paths to prevent the occurrence of hazardous mixtures of the gases. Good ventilation assists in this prevention together with the avoidance of open flames or sparking devices.

The aforementioned sequential or indexing of the negative electrodes 86 in relation to their associated transfer chamber 46 prevents possible cross-contamination of samples in the transfer chambers 46 if the electrode component 70 is removed and later reinstalled by the user during the process. The indexing or alignment keys 88 and 36 respectively provide this prevention.

The buffer 110 used has a high pH at between 7 and 8. A quantity of DEAE is placed in each transfer chamber 46 which serves as the exchange resin material 112. The exchange resin material 112 rests upon the filter 62 which serves as a support for the bed of exchange resin material 112, the latter being about 5 millimeters high. The transfer chamber 46 is essentially full of the buffer 110 solution to maintain the pH.

The location of the large charged molecules of interest, say it is a DNA fragment from an agarose or acrylamide gel, is identified by staining methods or radioactive tagging. Then that portion of the gel, including that zone or band, is cut out and then cut up into smaller pieces 114. Generally, the smaller the pieces of gel 114 are, the faster the action. The small pieces of gel 114 are then placed in the transfer chambers 46 below the surface of the buffer 110. Having the approximate same density as the buffer 110, the small pieces of gel 114 essentially float where they are placed in the buffer 110.

Actually, using a plurality of transfer chambers 46, a plurality of different bands of interest may be recovered independently without cross contamination.

When the apparatus 15 is fully assembled and the power is applied, the nucleic acid in the gel pieces 114, being negatively charged, is held by the electrode 86 and attracted towards the bottom of the transfer chamber 46. Thus the nucleic acid migrates out of the gel pieces 114, because of the electrical field operating on the gel pieces 114. Thereafter it migrates downwardly through the buffer 110 and starts through the DEAE exchange resin bed 112. The exchange resin bed 112 has a strong binding affinity for nucleic acids and so the nucleic acids are intercepted on the path toward the orifice 58 and bound to the exchange resin bed 112. Other large negatively charged molecules that might be there as contaminants are not bound to the exchange resin bed 112 and they migrate through and out of the transfer chamber 46.

After an elapsed time of operation, essentially one hour, but three hours is preferable to assure completion, the device is shut off and the transfer chambers 46 are removed. The exchange resin bed 112 with the bound molecules of nucleic acid is removed and the nucleic acid extracted and recovered by known methods, procedures, and techniques.

Numerous materials may be used for the structure of this invention, provided they are not subject to attack by the aforementioned materials and electrical action involved. Clear plastics is one substance for most elements unless otherwise provided herein, however, a black or dark color plastics may be desirable for the circular base 22, the circular support plate 32, the circular top plate 72, the circular carrier 94, the outer spacer ring 120, and the center spacer disc 122. The electrodes 82 and 86 are preferably platinum. The index or alignment keys 36 and 88 are preferably red. It is to be noted, however, that other suitable materials and colors are within the scope and intent of this invention.

It is to be noted that although a variation in geometrical configuration has been mentioned for the apparatus 15, a circular configuration is preferred and has been described herein. The circular configuration provides the most consistent electrical field possible between the centrally located positive electrode 82 and the plurality of radially placed negative electrodes 86 as to the path between the positive electrode 82 and each of the negative electrodes 86.

As can be readily understood from the foregoing description of the invention, the present structure can be configured in different modes to provide the ability to recover nucleic acids and other substances.

Accordingly, modifications and variations to which the invention is susceptible may be practiced without departing from the scope and intent of the appended claims.

What is claimed is:

1. An apparatus for the recovery of nucleic acids and other substances, comprising:
    a base container means;
    at least one transfer chamber means, said at least one transfer chamber means having a support means, said at least one transfer chamber means with said support means being removably inserted into said base container means, said at least one chamber means having a interior;
    a filter means, said filter means being suitably supported in at least one transfer chamber means; and
    an electrode means, said electrode means being removably assembled on to said base container means, said electrode means thereby being positioned for extending directly into said interior of said at least one transfer chamber means.

2. An apparatus for the recovery of nucleic acids and other substances as recited in claim 1 and additionally, a power supply means and a power source means, said power supply means being electrically connected to said electrode means and to said power source means.

3. An apparatus for the recovery of nucleic acids and other substances as recited in claim 2, wherein said electrode means has a positive electrode and at least one negative electrode, said positive and at least one negative electrodes being suitably electrically connected to said power supply means, said power source means providing direct current and being capable of adjusting the direct current voltage provided.

4. An apparatus for the recovery of nucleic acids and other substances as recited in claim 3, wherein said base container means consists of a base member, a first wall member, and a plurality of leg members, said base member being flat and having a top surface and a bottom surface, said first wall member having thickness, an outside surface and an inside surface, said first wall member being formed and configured into an enclosure with two open ends, said top surface of said base member being suitably affixed to one of said two open ends of said first wall member, said plurality of leg members being spaced apart and suitably affixed to said bottom surface of said base member, said base container means being liquid tight and capable of containing and holding a liquid.

5. An apparatus for the recovery of nucleic acids and other substances as recited in claim 4, wherein said at least one transfer chamber means with said support means consists of a flat plate-like member, a second wall member, a tube-like member, a washer-like member, an indexing means, and said at least one transfer chamber means, said flat plate-like member having a top surface and a bottom surface, said second wall member having thickness, an outside surface and an inside surface, said second wall member being formed and configured into an enclosure with two open ends, said bottom surface of said flat plate-like member being suitably affixed to one of said two open ends of said second wall member, said flat plate-like member having a first aperture centrally located therein and therethrough and at least one second aperture spaced radially from said first aperture, said at least one second aperture in said flat plate-like member being therein and therethrough, said tube-like member having a distal end and an inside diameter of the same diameter of said first aperture centrally located, said tube-like member having inside diameter thereof positioned to coincide with the periphery of said first aperture at said top surface of said flat plate-like member, said tube-like member being suitably affixed to said top surface of said flat plate-like member as positioned, said at least one transfer chamber means being removably and partially inserted into said at least one second aperture and being thereby supported, said tube-like member having a bevel on the outside periphery of the distal end thereof, said tube-like member having a groove spaced from said distal end thereof and located on the outside surface thereof, said washer-like member being flexible and rubber-like and removably affixed to said tube-like member in said groove, said washer-like member thereby being so positioned so as to partially rest upon said at least one transfer chamber means and thereby retain said at least one transfer chamber means in said at least one second aperture in said flat plate-like member, said indexing means being positioned and spaced radially on said top surface of said flat plate-like member from said first aperture and spaced circumferentially from said at least one transfer chamber, said indexing means being suitably affixed to said top surface.

6. An apparatus for the recovery of nucleic acids and other substances as recited in claim 5 and additionally, a plurality of additional transfer chamber means, and additional second apertures, said additional second apertures being each spaced radially from said first aperture and each spaced circumferetially from said at least one second aperture and from said indexing means, said additional transfer chamber means each being removably and partially inserted into a respective additional second aperture and partially under said flexible rubber-like and washer-like member, and additionally a plurality of index numerals, beginning with the numeral one and being located radially beside each said transfer chamber means sequentially starting at the first transfer chamber means adjacent to said indexing means.

7. An apparatus for the recovery of nucleic acids and other substances as recited in claim 6, wherein said at least one transfer chamber means and said plurality of additional transfer chamber means each consists of a first portion, a second portion, a third portion, a transition portion, and a filter means, each of said first, second, and third portions being cylindrical-like and tube-like with a passageway therethrough, said first portion being suitably affixed to said transition portion, said transition portion being tapered from a first diameter coinciding with the diameter of said first portion to a lesser diameter coinciding with the diameter of said second portion, said second portion being suitably affixed to said lesser diameter of said transition portion, the distal end of said second portion being partially closed circumferentially to form a partial floor-like bottom with an aperture therein and therethrough, said third portion being of a diameter coinciding with the diameter of said aperture in said partial floor-like bottom and being suitably affixed thereto, said third portion being orifice-like, said first and second portions having a plurality of ring-like marks spaced apart therearound, said filter means being removably inserted into said second portion and located upon said partial floor-like bottom.

8. An apparatus for the recovery of nucleic acids and other substances as recited in claim 7, wherein said electrode means consists of top plate member, a third wall member, an electrode carrier member, an electrode shield member, an indexing member, said power supply means, and said positive and negative electrodes, said top plate member being flat and having a top surface and a bottom surface, said third wall member having thickness, an outside surface and an inside surface, said third wall member being formed and configured into an enclosure with two open ends, said bottom surface of said top plate member being suitably affixed to one of said two open ends of said third wall member, said top plate member having a plurality of apertures therein and therethrough, one of said plurality of apertures providing for access therethrough of said power supply means, said power supply means being suitably affixed to said top plate member with a suitable restraining means, with the balance of said plurality of apertures in said top plate member serving as vents for the escape of gases, said electrode carrier member having a negative electrode holding means, a positive electrode holding means, and a ring-like spacer means, said negative electrode holding means having a centrally located aperture therein and therethrough and a circumferential trough-like groove in the uppermost surface thereof, said at least one negative electrode and additionally a plurality of additional negative electrodes being spaced radially from said centrally located aperture in said negative electrode holding means and spaced circumferentially around and in said trough-like groove, said negative electrodes extending through the bottom of said trough-like groove to extend below the lowermost surface of said negative electrode holding means, said positive electrode passes through said positive electrode holding means to extend below the lowermost surface thereof, said plurality of negative electrodes being suitably electrically connected together in said trough-like groove and sealed in place by an epoxy-type means, said suitably electrical connection of said plurality of negative electrodes and said positive electrode being suitably electrically connected to said power supply means, said positive electrode holding means being centrally located over said central aperture in said negative electrode holding means and suitably affixed to the uppermost side of said negative electrode holding means, said ring-like spacer means being of the same peripheral configuration as said negative electrode holding means and suitably affixed to the uppermost side of said negative electrode holding means and then suitably affixed to the lowermost side of said top plate member, an aperture being provided in and through said positive electrode holding means to communicate as a vent means with one of said apertures in said top plate member, with the balance of said apertures serving as vent means communicating on the inside of said top plate member at a position on the exterior of said electrode carrier member and said ring-like spacer means, said electrode shield member being tube-like and open at each end with a passageway therethrough, said electrode shield member being located around said positive electrode and encompassing said vent through said positive electrode holding means and being suitably affixed to said positive electrode holding means, said indexing member being located so as to fit between two adjacent transfer chamber means and suitably affixed to the undermost side of said electrode carrier member, said indexing member being used to align said electrode means when being removably assembled on said base container means by aligning said indexing member with said indexing means.

9. An apparatus for the recovery of nucleic acids and other substances as recited in claim 7, wherein said base container means, said transfer chamber means support means, and said electrode means are all circular in configuration, said circular configuration being achieved by said base member and said formed enclosure of said first wall member being circular in configuration, said flat plate-like member and said formed enclosure of second wall member being circular in configuration, and said top plate member, said formed enclosure of third wall member, said electrode carrier member and said ring-like spacer means being circular in configuration.

10. An apparatus for the recovery of nucleic acids and other substances, comprising:
 a base container means;
 at least one transfer chamber means, said at least one transfer chamber means being removably inserted into said base container means; an electrode means positioned in said transfer chamber means, the structure of which extends directly into the interior of said transfer chamber means; and
 a filter means, said filter means being suitably supported in at least one transfer chamber means.

* * * * *